United States Patent
Huang et al.

(10) Patent No.: US 11,249,204 B2
(45) Date of Patent: Feb. 15, 2022

(54) RADIATION IMAGE DETECTOR AND MANUFACTURE METHOD THEREOF

(71) Applicant: IRAY TECHNOLOGY COMPANY LIMITED, Shanghai (CN)

(72) Inventors: Zhongshou Huang, Shanghai (CN); Tieer Gu, Shanghai (CN)

(73) Assignee: IRAY TECHNOLOGY COMPANY LIMITED, Shanghai (CN)

( * ) Notice: Subject to any disclaimer, the term of this patent is extended or adjusted under 35 U.S.C. 154(b) by 0 days.

(21) Appl. No.: 17/017,374

(22) Filed: Sep. 10, 2020

(65) Prior Publication Data

US 2021/0223417 A1 Jul. 22, 2021

(30) Foreign Application Priority Data

Jan. 21, 2020 (CN) .......................... 202010072660.6

(51) Int. Cl.
*G01T 1/24* (2006.01)
*G01T 1/20* (2006.01)
*A61B 6/00* (2006.01)

(52) U.S. Cl.
CPC ............ *G01T 1/241* (2013.01); *G01T 1/2018* (2013.01); *A61B 6/486* (2013.01)

(58) Field of Classification Search
CPC ........ G01T 1/241; G01T 1/2018; A61B 6/486
See application file for complete search history.

(56) References Cited

U.S. PATENT DOCUMENTS 6,133,687 A * 10/2000 Clarke ................. G02B 3/0037
313/478
6,472,665 B1 10/2002 Ishisaka et al.
(Continued)

FOREIGN PATENT DOCUMENTS

| EP | 1715361 A1 | 10/2006 |
|---|---|---|
| JP | H5244506 A | 9/1993 |
| JP | 2008304349 A | 12/2008 |

OTHER PUBLICATIONS

Extended European Search Report for Application No. 20211625.7, dated Apr. 21, 2021.
(Continued)

*Primary Examiner* — Kiho Kim
(74) *Attorney, Agent, or Firm* — W&G Law Group (57) ABSTRACT

Embodiments of the present invention provide a radiation image detector and a manufacture method to produce the radiation image detector. The radiation image detector includes: a radiation conversion layer, configured to convert a radiation image into a visible light image; an image sensing layer for visible light, including a pixel array formed by a plurality of photosensitive pixels, configured to detect the visible light image; and a microlens layer, disposed between the radiation conversion layer and the image sensing layer, the microlens layer including a lens array formed by multiple micro convex lenses, and optical axes of the micro convex lenses being perpendicular to the image sensing layer. In addition, both the radiation conversion layer and the microlens layer have curved surface structures that are bended in the same direction that non-parallel radiations, emitted from an X-ray generator, will impinge perpendicularly on the radiation conversion layer.

8 Claims, 7 Drawing Sheets

(56) References Cited

U.S. PATENT DOCUMENTS

| | | | | |
|---|---|---|---|---|
| 6,476,394 | B1* | 11/2002 | Amitani | G01T 1/2018 250/368 |
| 6,528,796 | B1* | 3/2003 | Kaifu | G01T 1/2018 250/370.09 |
| 7,135,686 | B1* | 11/2006 | Grady | G01T 1/2018 250/370.11 |
| 2010/0140487 | A1* | 6/2010 | Barrett | G01T 1/1642 250/366 |
| 2011/0198503 | A1* | 8/2011 | Koren | G01T 1/2018 250/362 |
| 2012/0294416 | A1* | 11/2012 | Ashokan | H01L 27/14627 378/19 |
| 2014/0145085 | A1* | 5/2014 | Wu | G01T 1/2018 250/366 |
| 2014/0151564 | A1* | 6/2014 | Brouard | G01T 1/2018 250/362 |
| 2014/0264043 | A1 | 9/2014 | Ganguly et al. | |
| 2014/0326892 | A1* | 11/2014 | Ootorii | H01L 27/14663 250/366 |
| 2016/0049441 | A1* | 2/2016 | Shieh | H01L 27/14612 257/43 |
| 2016/0054456 | A1* | 2/2016 | Lebrun | G01T 1/2018 250/366 |
| 2017/0234992 | A1* | 8/2017 | Miyazawa | H01L 27/14625 257/432 |
| 2019/0049599 | A1* | 2/2019 | Matsumoto | H01L 23/5387 |

OTHER PUBLICATIONS

Eijk Carel W E Van: "Inorganic scintillators in medicalimaging,", Physics in Medicine and Biology, vol. 47, No. 8, Apr. 5, 2002, pp. R85-R106, XP055793564, Briston GB ISSN: 0031-9155, DOI: 10.1088/0031-9155/47/8/201. Retrieved from the Internet: URL: https://www.researchgate.net/profile/Cwe-Eijk/publication/11341075_Inorganic_Scintillators_in_Medical_Imaging/links/02e7e52b8a42990643000000/Inorganic-Scintillators-in-Medical-Imaging.pdf.

* cited by examiner

RADIATION IMAGE DETECTOR AND MANUFACTURE METHOD THEREOF

CROSS-REFERENCE TO RELATED APPLICATIONS

The present invention is based upon and claims the benefit of priority of Chinese Patent Application No. 202010072660.6, filed on Jan. 21, 2020, the entire contents of which is incorporated herein by reference.

TECHNICAL FIELD

The present invention relates to the field of image detection, and in particular, to a radiation image detector and a manufacture method to produce the radiation image detector.

BACKGROUND

Flat panel radiation image detectors have been widely used to monitor digital medical diagnosis and radiation therapy in real time. Compare with conventional radiation image detectors, such detectors have relatively a high speed, a low cost, a low exposure, high image quality, and perhaps other advantages. They are convenient for data storage, transmission, and operation, and can be integrated into digital medical systems. The development of TFT-LCD and solar cell technologies has made dynamic X-ray imaging on the flat panel radiation image detector feasible. The dynamic X-ray imaging is not only used in applications of large size medical images, such as chest fluoroscopy and cardiovascular examinations, but also have been gradually adopted in dentistry and other application fields where small areas are regions of interest for diagnosis via imaging.

The flat panel radiation image detectors can be classified into direct conversion detectors and indirect conversion detectors by detection principle and structure. An indirect conversion detector mainly includes a radiation conversion layer and an optical image detector. The radiation conversion layer can convert radiations into visible light, and the optical image detector includes multiple optoelectric converters. Electron-hole pairs are generated when the visible light is impinging on the optoelectric converters. The electron-hole pairs are separated by an electric field. The separated electrons and holes subsequently move to anodes and cathodes of the optoelectric converters, respectively, and are stored there. As such, electrical signals are generated and output to an external circuit, and finally X-ray image acquisition is completed.

In a radiation imaging system, radiations such as X-rays are generated and emitted by an X-ray generator, commonly referred to as an X-ray tube, which is in vacuum condition during operation. When an electron beam is accelerated by a strong electric field and bombarded on a metal target, the bombardment of high-speed electrons on metal atoms causes the atoms to emit X-ray according to a theory of bremsstrahlung radiation. X-rays are emitted from the metal target, pass through an output window, and irradiate a human body through a series of collimators and energy filters. Some unabsorbed X-rays irradiate on a flat panel X-ray image detector positioned right behind the human body. The X-ray image detector first converts the X-rays into a visible light image, and then obtains an electronic image through a visible light image detector.

Along the whole journey from emission from the X-ray tube to interaction with the X-ray detector, the X-ray beam is continuously diffused in a divergent manner, starting from a focal point where the electron bombardment occurred. As consequence, X-ray photons impinging on the X-ray image detector in various oblique angles. The luminance and resolution of an image obtained will gradually vary from the center to borders of the X-ray image detector. Due to a magnification effect originated from divergent X-ray beams, the image is distorted at edges of the detector. Therefore, it is a primary objective of this invention to provide a solution at a device level and at a system level to tackle these problems.

SUMMARY

The above objective is achieved by providing a radiation image detector having a curvature surface conforming to the X-ray beam divergence, as well as a manufacture method to make the radiation image detector.

According to one embodiment, a radiation image detector comprises:

a radiation conversion layer, configured to convert a radiation image into a visible light image;

an image sensing layer for visible light, including a pixel array formed by a plurality of photosensitive pixels, configured to detect the visible light image; and a microlens layer, disposed between the radiation conversion layer and the image sensing layer, the microlens layer including a lens array formed by a plurality of a plurality ofity of micro convex lenses, and optical axes of the micro convex lenses being perpendicular to the image sensing layer; the radiation conversion layer, the microlens layer, and the image sensing layer all having curved surface structures which conform to each other and bending in one direction.

According to another embodiment, a manufacture method for a radiation image detector comprises:

manufacturing a radiation conversion layer on a first substrate, the radiation conversion layer being configured to convert a radiation image into a visible light image;

manufacturing an image sensing layer for visible light on a second substrate, the image sensing layer including a pixel array formed by a plurality of a plurality ofity of photosensitive pixels, and being configured to detect the visible light image;

manufacturing a light shielding structure and a lens array on the image sensing layer; and bending, covering, and laminating the first substrate and the second substrate.

The first substrate and the second substrate conform to each other in terms of bending direction and bending shape.

The radiation conversion layer and the image sensing layer both have curved surface structure and conform to the divergent X-ray beam in a manner that X-rays impinge on the radiation layer at an angle that is substantially perpendicular to the curved surface of the radiation conversion layer. As results, uniform spatial resolution and sensitivity across the entire area of the radiation detector can be achieved.

BRIEF DESCRIPTION OF DRAWINGS

To describe the technical solutions in the embodiments of the present invention more clearly, the following briefly describes the accompanying drawings required for the embodiments. Clearly, the accompanying drawings in the following description show merely some embodiments of the present invention. It can be assumed that a person skilled in the art can extend and derive similar component structures and manufacturing methods based on the component structures and concepts disclosed in the embodiments of the present invention, and these similar component structures and manufacturing methods undoubtedly fall within the scope of the claims of the present invention.

DESCRIPTION OF EMBODIMENTS

For better understanding of the technical solutions of the present invention, the following describes the embodiments of the present invention in detail with reference to the accompanying drawings.

The terms used in the embodiments of the present invention are merely for the purpose of illustrating specific embodiments, and are not intended to limit the present invention. The terms "a" and "the" of singular forms used in the embodiments and the appended claims of the present invention are also intended to include multiple forms, unless otherwise specified in the context clearly.

The term "and/or" in the present invention describes only an association relationship for describing associated objects and represents that three relationships can exist. For example, A and/or B can represent the following three cases: Only A exists, both A and B exist, and only B exists. In addition, the character "/" in this specification generally indicates an "or" relationship between the associated objects.

In the description of the present invention, it should be understood that, terms such as "basically", "approximately", "around", "about", "roughly", and "generally" described in the claims and embodiments of the present invention indicate values generally recognized within a reasonable process operation range or tolerance range, rather than exact values.

The inventor of the present invention conceives solutions to the problems in the prior art through detailed in-depth study.

Figure 1:
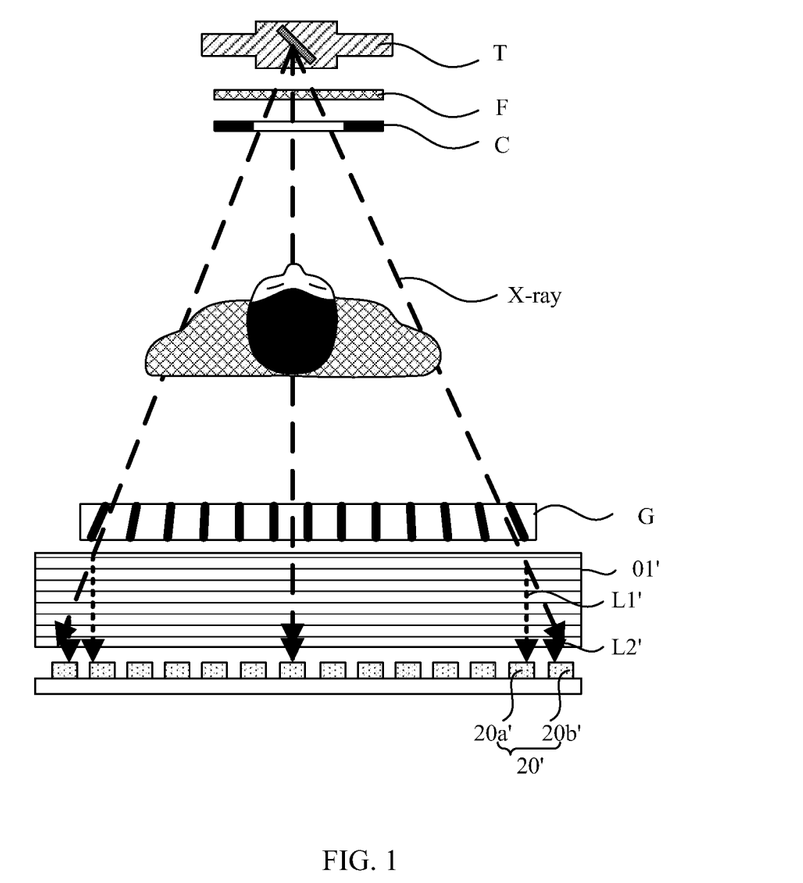
FIG. 1 is a working principle diagram of a radiation image detector in the prior art.

FIG. 1 is a working principle diagram of a radiation image detector in the prior art. As shown in FIG. 1, a radiation generator T emits radiations (X-rays), which form radiation beams with more concentrated energy and angles after passing through an energy filter F and a collimator C, and enter a part to be checked of a human body. Radiations passing through human tissue are absorbed and scattered, so that energy of the radiations is attenuated. Radiations of different attenuation degrees can reflect different conditions of the human tissue. Therefore, the radiations passing through the human tissue carry various information of the human tissue. The radiations passing through the human tissue further pass through a metal grid G used for collimation. As a result, large-angle radiations generated by scattering inside the human body are filtered out, and the remaining radiations enter a flat panel radiation image detector.

The radiation image detector shown in FIG. 1 includes a radiation conversion layer 01' and photosensitive pixels 20'. A scintillator in the radiation conversion layer 01' generates visible light photons under excitation by radiations. The photosensitive pixels 20' generate an electrical signal caused by photo-generated electrons or holes after receiving the visible light photons. However, because the radiation beams from the radiation generator are projected to the human body and the following flat panel radiation image detector at divergent angles, as shown in FIG. 1, there are specific included angles between the normal direction of the radiation conversion layer 01' and the radiations incident to the radiation image detector. Consequently, the length of a radiation's path for passing through the radiation conversion layer 01' is related to the position of the flat panel image detector. Photons of visible light excited by a tilted radiation on its path are distributed on a path that has a specific included angle with the normal direction of the radiation conversion layer 01'. In other words, not all of the photons of the visible light excited by the tilted incident radiation are right above corresponding photosensitive pixels 20', but are diffused laterally by a certain distance. Consequently, an X-ray photon finally produces a long light spot with a certain width. Such a long light spot is received by a series of photosensitive pixels on an image detection array, and an image is blurred or loses details. As shown in FIG. 1, visible light L1' and L2' excited by the tilted radiation on the right side are respectively received by photosensitive pixels 20a' and 20b'.

Because the visible light excited by the tilted radiation is received by another photosensitive pixel 20' in addition to its corresponding photosensitive pixel 20', an image signal contributed by this part of visible light is overlaid on an original image signal of the another photosensitive pixel 20', causing crosstalk or blur to an image and reducing the value of a spatial modulation transfer function (MTF) of the image.

A solution in the prior art for improving an image's MTF effect is to use a scintillator in an amorphous state to manufacture the radiation conversion layer 01', for example, cesium iodide CsI(Tl) or CsI(Na). A columnar crystal structure that can direct visible light can be formed through evaporation at a certain angle or through tiny periodic convex structures on a substrate, so that most of visible light emitted by luminous points can be directed to photosensitive pixels 20' right below. However, a scintillator manufactured by evaporation in the prior art is highly sensitive to humidity and temperature, which affects performance stability of the image detector. Besides, crystal types for the scintillator are also limited to some extent in this manufacture manner. In addition, even if the radiation conversion layer 01' is manufactured by a scintillator of the columnar crystal structure, only the visible light emitted by the luminous points is directed to the photosensitive pixels 20' right below, and a luminous point excited by a tilted incident radiation is still deviated from a position right above its corresponding photosensitive pixel 20'.

For the problems in the prior art, an embodiment of the present invention provides a radiation image detector, which can be applied to various crystal types of scintillators, and can reduce crosstalk, improve the image's MTF effect, or improve detection quantum efficiency at high spatial frequencies.

Figure 2:
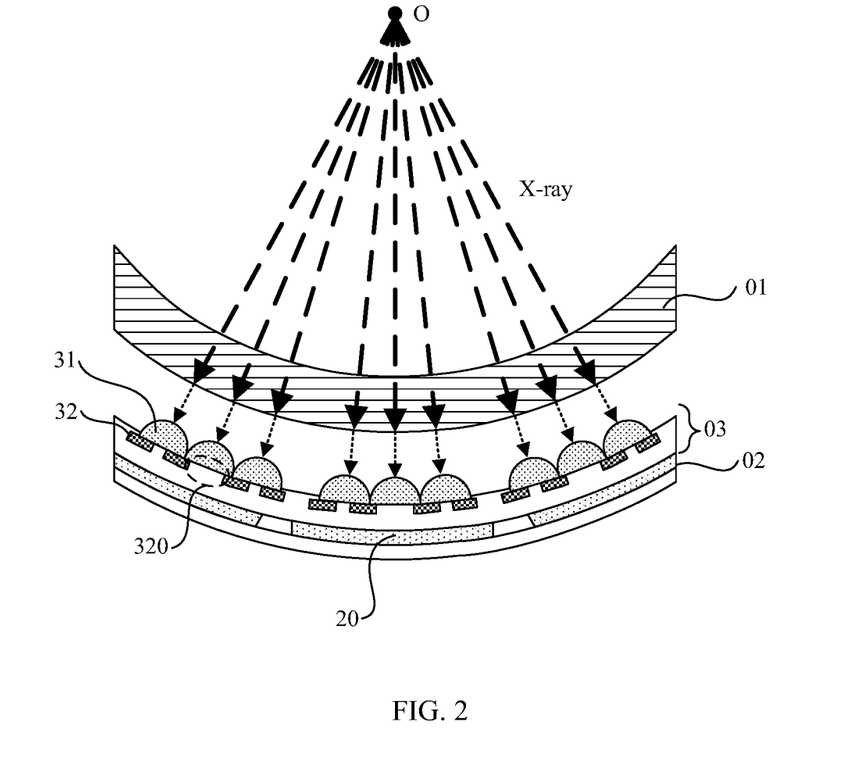
FIG. 2 is a schematic cross-sectional diagram of a radiation image detector according to an embodiment of the present invention.

FIG. 2 is a schematic cross-sectional diagram of a radiation image detector according to an embodiment of the present invention.

As shown in FIG. 2, the radiation image detector provided in the embodiment of the present invention includes a radiation conversion layer 01, a layer 02 to detect a visible light image, and a microlens layer 03.

The radiation conversion layer 01 is configured to convert a radiation image into a visible light image. Based on their energy distributions, radiations can be X-rays of 1 KeV to hundreds of KeV or γ (Gamma) rays with energy radiation higher than 1 MeV. The radiation conversion layer 01 includes films or crystals of scintillators or phosphors, for example, films or crystals of cesium iodide CsI(Tl) doped with thallium, or films or crystals of a material that can convert radiations into visible light, such as cadmium tungstate (CdWO4) or gadolinium oxysulfide scintillator (GOS, Gd2O2S:Pr).

The layer 02 to detect a visible light image includes a pixel array formed by a plurality of photosensitive pixels 20, and is configured to detect the visible light image. "A plurality of" is understood as "multiple". That is, the pixel array formed by photosensitive pixels 20 includes multiple photosensitive pixels 20. In addition, adjacent photosensitive pixels 20 are isolated through etching, an insulating film, or the like, to prevent signal crosstalk between different photosensitive pixels 20 and interference noise of driving pulses. Optionally, the photosensitive pixel 20 includes an optoelectric converter, and the optoelectric converter can be a photodiode.

The microlens layer 03 is disposed between the radiation conversion layer 01 and the layer 02 to detect a visible light image. The microlens layer 03 includes a lens array formed by a plurality of micro convex lenses 31, and optical axes of the micro convex lenses 31 are perpendicular to the layer 02 to detect a visible light image. That is, the lens array formed by micro convex lenses 31 includes multiple micro convex lenses 31. The micro convex lenses 31 in the microlens layer 03 can concentrate light, and are configured to concentrate visible light that is emitted by the radiation conversion layer 01 and near the optical axes to corresponding photosensitive pixels 20.

In addition, the radiation conversion layer 01, the microlens layer 03, and the layer 02 to detect a visible light image all have curved surface structures which conform to each other and bending in one direction. Still referring to FIG. 2, a radiation emitting source emits divergent radiations. The radiation conversion layer 01, the microlens layer 03, and the layer 02 to detect a visible light image all have curved surface structures which conform to each other, and bending directions of the three layers all face an incident direction of the radiations. Optionally, the three curved surface structures each can be a part of a spherical surface, and centers of sphere for the spherical surfaces corresponding to the three curved surface structures basically overlap. Moreover, as shown in FIG. 2, when the radiation emitting source emits divergent radiation beams, the center of sphere is roughly located in a position, on a metal target of a radiation tube, bombarded by an electron beam.

Radiations received by a radiation image detector that uses such a curved surface structure are projected perpendicularly into the radiation image detector except for a few radiations that encounter relatively large deflection in their forward directions due to scattering. In addition, the normal line of each photosensitive pixel 20 of the radiation image detector that uses such a curved surface structure is basically parallel to the incident direction of the radiations. In this way, the center of a diffuse spot of photons of excited visible light is always right above a corresponding photosensitive pixel 20, thereby significantly reducing lateral diffusion of the photons of the visible light and increasing a spatial resolution of an image.

Figure 3:
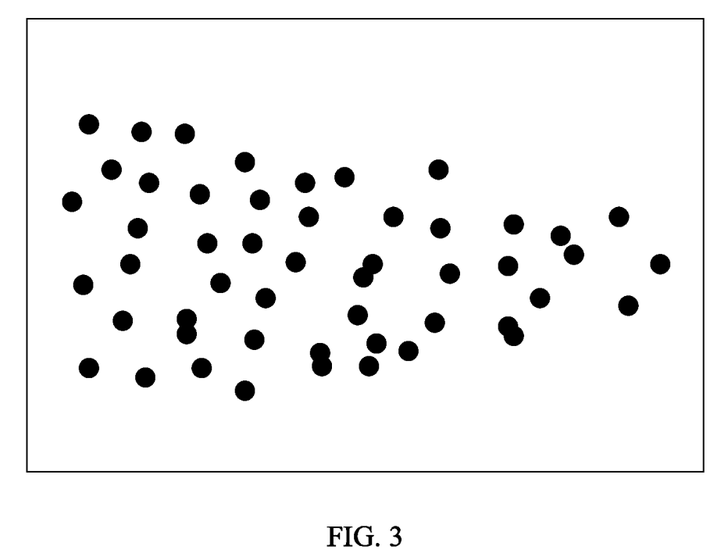
FIG. 3 is a diagram of a photon distribution of a flat panel radiation image detector in the prior art.
Figure 4:
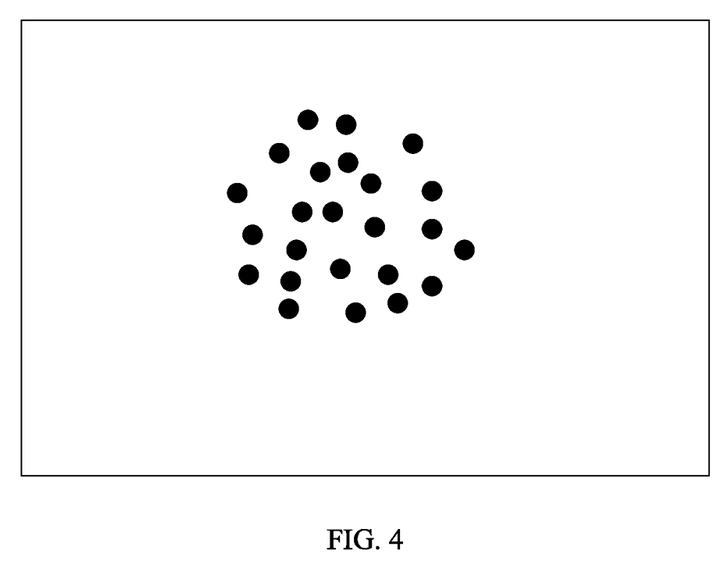
FIG. 4 is a diagram of a photon distribution of a radiation image detector on a curved surface according to an embodiment of the present invention.

FIG. 3 is a diagram of a photon dispersion distribution generated after a point-source radiation is incident on a flat panel image detector in the prior art. FIG. 4 is a diagram of a photon dispersion distribution generated by a radiation image detector on a curved surface according to an embodiment of the present invention. It can be found from the comparison between FIG. 3 and FIG. 4 that, when the same radiation beam is detected, light spots generated through the flat panel radiation image detector in the prior art are more dispersedly distributed, and light spots generated through the radiation image detector on a curved surface provided in the embodiment of the present invention are more concentratedly distributed. This significant difference between the diffusion functions for the two types of detectors makes the radiation image detector provided in the embodiment of the present invention have a higher spatial resolution.

Still referring to FIG. 2, in an embodiment of the present invention, the microlens layer 03 further includes a light shielding structure disposed on a side thereof close to the layer 02 to detect a visible light image. The light shielding structure includes at least one light shielding layer 32, the light shielding layer 32 includes a plurality of through holes 320, and the through holes 320 one-to-one correspond to the micro convex lenses 31. Only one light shielding layer 32 is used for illustration in the figure. The quantity of through holes 320 in this light shielding layer 32 is not specifically limited in the present invention. In the embodiment of the present invention, the light shielding structure can alternatively include N light shielding layers 32, and N is an integer ranging from 1 to 3.

In this embodiment of the present invention, the light shielding layer 32 and the micro convex lenses 31 are located between the radiation conversion layer 01 and the photosensitive pixels 20. The micro convex lenses 31 can concentrate small-angle light near the optical axes to positions of the through holes 320 in the light shielding layer 32, and the light is subsequently transmitted to the photosensitive pixels 20 to contribute to an image signal. In addition, the light shielding layer 32 can shield large-angle light to prevent visible light from being incident on a photosensitive pixel 20 in a deviated position, thereby further reducing crosstalk. The large-angle light that can be shielded by the light shielding layer 32 includes not only light emitted from the radiation conversion layer 01 corresponding to photosensitive pixels 20 around, but also some large-angle light emitted from the right-above radiation conversion layer 01 corresponding to the micro convex lenses 31 (that is, large-angle light near the optical axes of the convex lenses). In other words, a combination of the light shielding layer 32 and the micro convex lenses 31 forms an optical collimator.

Figure 5:
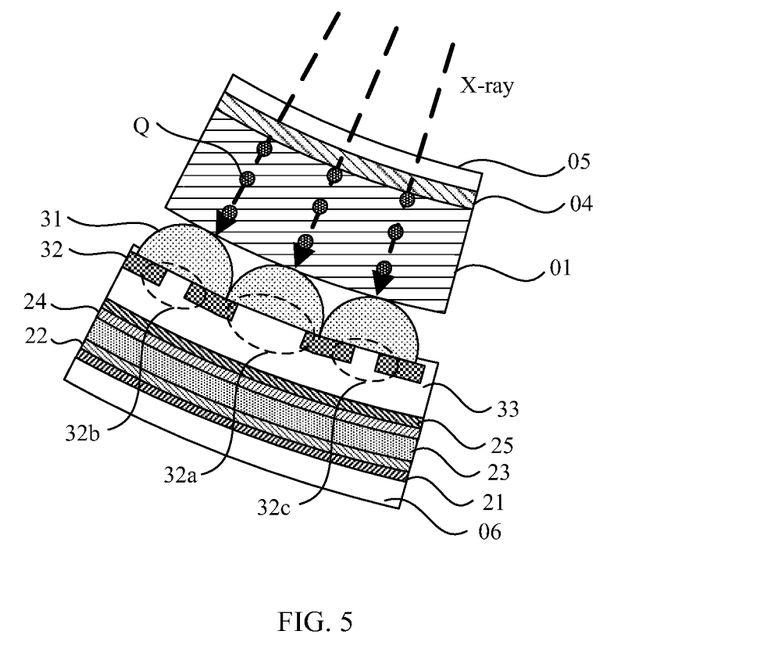
FIG. 5 is a locally enlarged diagram of a radiation image detector according to an embodiment of the present invention.

The following describes in detail the radiation image detector provided in the embodiment of the present invention with reference to the accompanying drawings. FIG. 5 is a locally enlarged diagram of a radiation image detector according to an embodiment of the present invention. FIG.

5 shows a locally enlarged diagram of a radiation image detector corresponding to one photosensitive pixel 20.

The radiation image detector shown in FIG. 5 further includes a cover 05 and a reflection layer 04. The reflection layer 04 is located on a side, of the radiation conversion layer 01, away from the layer 02 to detect a visible light image, and the cover 05 is located on a side, of the reflection layer 04, away from the radiation conversion layer 01. The cover 05 can be made from a material easily penetrated by radiations, for example, a carbon fiber sheet or an aluminum alloy sheet. The reflection layer 04 can be made from a material easily penetrated by radiations and highly reflective to visible light, for example, a film or powder of aluminum or silver. Photon radiation of the visible light generated by the radiation conversion layer 01 is emitted in various directions at an equal probability. Light radiated upward is turned back after being reflected by the reflection layer 04 at the top part and stands a chance to finally enter the photosensitive pixel 20 together with originally downwardly emitted photons, so as to generate an electrical signal caused by photo-generated electrons or holes.

In addition, the photosensitive pixel 20 shown in FIG. 5 can be a photodiode. As shown in the figure, the photosensitive pixel 20 includes a first electrode 21, a first doped layer 22, an optoelectric conversion layer 23, a second doped layer 24, and a second electrode 25 that are stacked successively on a second substrate 06. When the first electrode 21 is an anode, the first doped layer 22 is a P-type doped layer. In this case, the second electrode 25 is a cathode, and the second doped layer 24 is an N-type doped layer. When the first electrode 21 is a cathode, the first doped layer 22 is an N-type doped layer. In this case, the second electrode 25 is an anode, and the second doped layer 24 is correspondingly a P-type doped layer.

As shown in FIG. 5, one photosensitive pixel 20 corresponds to multiple micro convex lenses 31 and multiple through holes 320, and the micro convex lenses 31 one-to-one correspond to the through holes 320. An optical axis of each micro convex lens 31 communicates with its corresponding through hole 320. With this design, one photosensitive pixel 20 corresponds to multiple micro convex lenses 31. Therefore, the size of the micro convex lens 31 is far less than the size of the photosensitive pixel 20, which brings more convenience to film coating and curing processes. In addition, when a microlens array is smaller than the pixel, light can be well collimated even when the micro convex lenses 31 are not precisely aligned with the photosensitive pixel 20 during manufacture. For example, the foregoing light concentration and collimation effects can also be achieved by directly or indirectly covering an optical image detection array through a separate array panel including micro convex lenses and through holes or even a flexible film including microlenses and through holes. In particular, using a flexible film including micro convex lenses and through holes can facilitate manufacture of a radiation image detector with a certain curved surface.

In addition, in related technologies, due to a large area and a signal-to-noise ratio of an image, pixel sizes of radiation image detectors commonly used in medical applications are all greater than 50 µm. Pixel sizes are generally set to 100 µm for mammography x-ray detectors, and set to about 200 µm for image detectors used for radiographic diagnosis and medical applications on cardiovascular, thoracic, and other body parts. Based on basic principles and designs of optical lenses, a lens' height should be in one order of magnitude or basically the same as its diameter regardless of whether the lens is convex or concave. A larger lens size indicates more difficult manufacture. A process for manufacturing a 50 µm or even 100 µm high convex lens on a substrate with a large area, for example, 200 mm×200 mm, is very complex and difficult. In addition, adverse impact caused by the lens manufacture process on the optoelectric conversion layers in the photosensitive pixel is unpredictable.

In the embodiment of the present invention, subject to the size of the photosensitive pixel 20 and the diameter of the micros convex lenses 31, at least four micro convex lenses 31 can be disposed on one photosensitive pixel 20. In an optional manufacture method, an organic film is first coated. Then, a part of a solvent is evaporated in UV curing mode. Subsequently, the organic film is etched to form a stepped structure. Afterwards, the organic film is baked at a high temperature, so that arc shapes are formed at edges of the stepped structure due to softening flowability of the organic film layer, thereby forming a structure of the micro convex lens. Generally, the radius or the height of the micro convex lens 31 is several to more than ten microns based on capabilities of the processes such as film coating, UV curing or thermal curing, and etching. For detectors widely used for X-ray mammography diagnosis, 16 micro convex lenses 31 with a diameter of 10 µm may need to be placed on one 50 µm×50 µm pixel. Based on the structure provided in the embodiment of the present invention, multiple micro convex lenses 31 can be disposed on each photosensitive pixel 20 with simple processes and little manufacture difficulty.

In addition, still referring to FIG. 2 and FIG. 5, the radiation conversion layer 01, the microlens layer 03, and the layer 02 to detect a visible light image all have curved surface structures which conform to each other. The curved surface structures corresponding to the three layers each is a part of a spherical surface. In this case, curvature radiuses corresponding to the three layers are basically the same. Moreover, when incident radiations are divergent, a radiation emitting source is disposed in the position of the center of sphere corresponding to the curved surface structures of the radiation conversion layer 01, the microlens layer 03, and the layer 02 to detect a visible light image. This can ensure that the radiations emitted by the radiation emitting source are perpendicularly incident on the radiation conversion layer 01, and paths for transmitting the radiations in the radiation conversion layer 01 are perpendicular to the microlens layer 03 and the layer 02 to detect a visible light image. Therefore, a luminous point generated by a radiation beam by exciting a scintillator is projected as a symmetrical diffuse spot at the layer 02 to detect a visible light image.

The radiation conversion layer 01, the microlens layer 03, and the layer 02 to detect a visible light image are successively disposed along the paths for transmitting the radiations. That is, distances from the radiation emitting source to the radiation conversion layer 01, the microlens layer 03, and the layer 02 to detect a visible light image successively increase. Therefore, to ensure that the centers of sphere for the spherical surfaces corresponding to the three layers all correspond to the radiation emitting source, the curvature radiuses of the three layers should successively increase. However, considering that the distance between the radiation image detector and the radiation emitting source is relatively long, the curvature radiuses of the three layers are designed to be very similar; in other words, the curvature radiuses of the radiation conversion layer 01, the microlens layer 03, and the layer 02 to detect a visible light image are basically the same. In addition, the radiation image detector can be considered as a whole relative to the radiation emitting source. When it is ensured that the radiations emitted by the radiation emitting source are perpendicularly incident on the radiation image detector, a curvature radius of the radiation image detector is determined, and all of the respective curvature radiuses of the radiation conversion layer 01, the microlens layer 03, and the layer 02 to detect a visible light image in the radiation image detector can be considered to be basically the same as the curvature radius of the radiation image detector.

Figure 6:
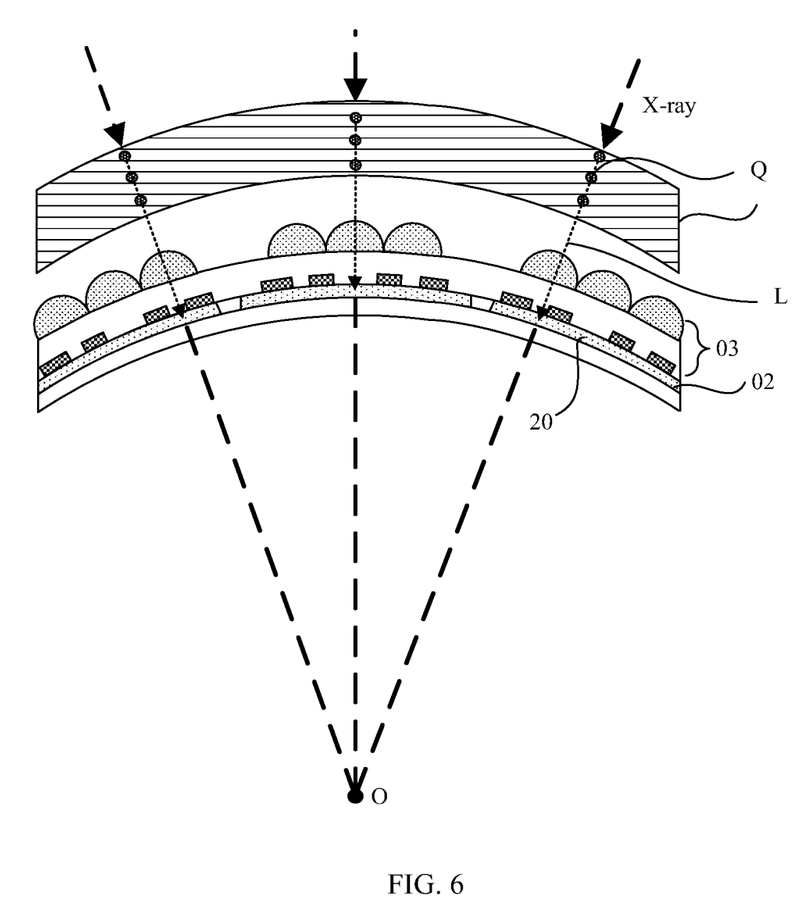
FIG. 6 is a schematic cross-sectional diagram of a radiation image detector according to another embodiment of the present invention.

It should be noted that, the radiation image detectors shown in FIG. 2 and FIG. 5 are both described by taking an example in which the radiation emitting source emits divergent radiations. However, in actual application scenarios, the radiation emitting source can alternatively emit convergent radiation beams. The radiation image detector provided in the embodiment of the present invention can also be applied to a case with incident radiations being convergent. FIG. 6 is a schematic cross-sectional diagram of a radiation image detector according to another embodiment of the present invention. As shown in FIG. 6, a radiation conversion layer 01, a microlens layer 03, and a layer 02 to detect a visible light image all have curved surface structures which conform to each other and bending in one direction, and bending directions of the three layers all face an emission direction of the radiations. Optionally, the three curved surface structures each can be a part of a spherical surface, and the centers of spheres for the spherical surfaces corresponding to the three curved surface structures overlap. In addition, as shown in FIG. 6, when a radiation emitting source emits convergent radiations, the center of sphere for the spherical surfaces is disposed in the position of a virtual focal point on a side, of the image detector, away from a radiation tube.

It can be learned from the foregoing analysis that, regardless of whether the incident radiations are divergent or convergent, the center of sphere for the spherical surfaces corresponding to the three curved surface structures basically overlaps the position of a focal point O of the incident radiations, and the focal point O of the incident radiations is an actual or virtual intersection point of any two incident radiations. In addition, the curvature radiuses of the three curved surface structures should also be roughly equal to the distance from the radiation conversion layer 01 to the focal point O of the incident radiations, to ensure that the incident radiations can be perpendicular to the radiation conversion layer 01.

The radiation image detector provided in the embodiment of the present invention is an image detector on a curved surface, and each functional film layer in the radiation image detector should also be a curved surface structure. As described above, the radiation conversion layer 01, the microlens layer 03, and the layer 02 to detect a visible light image all have curved surface structures which conform to each other, and the curved surface structures corresponding to the three layers each is a part of a spherical surface. However, even if the microlens layer 03 is a curved surface structure, the center of a through hole 320 in a light shielding layer 32 included in the microlens layer 03 should also overlap an optical axis of a corresponding micro convex lens 31.

Figure 7:
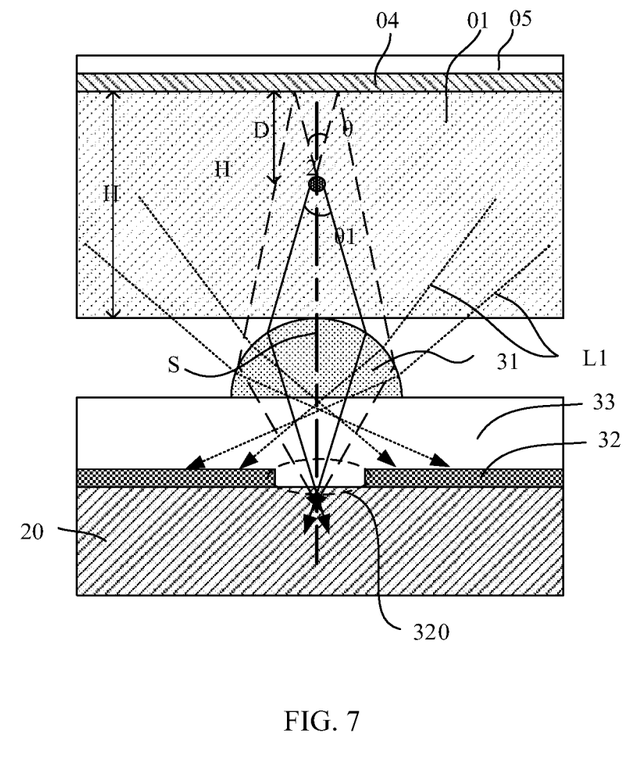
FIG. 7 is a working principle diagram of a radiation image detector according to an embodiment of the present invention.

FIG. 7 is a working principle diagram of a radiation image detector according to an embodiment of the present invention. FIG. 7 is only a simplified schematic diagram. The thickness of the radiation conversion layer 01 is H. Because the radiations are perpendicularly incident on the radiation conversion layer 01, transmission directions of the radiations are perpendicular to the thickness direction of the radiation conversion layer 01. The incident radiations excite a scintillator to generate photons of visible light after entering the radiation conversion layer 01. One radiation may excite the scintillator to generate multiple photons of visible light, and positions in which the photons of visible light are generated (that is, luminous points) are substantially located on a path traveled by the radiation in the radiation conversion layer 01. For example, visible light is obtained through conversion in a position at a depth of DH in the radiation conversion layer 01. In visible light emitted in all directions, light emitted downward within a conical solid angle $\theta 1$ can pass through a through hole 320 in the light shielding layer 32 after being acted on by a micro convex lens 31, and finally reach a position, in a photosensitive pixel 20, in which the visible light is concentrated to the through hole 320, and the through hole 320 is equivalent to an aperture; and light emitted upward within a conical solid angle $\theta 2$ can be reflected by a reflection layer 04, and then successively pass through the micro convex lens 31 and the through hole 320 in the light shielding layer 32 and reach the photosensitive pixel 20. Light L1 having a large included angle with an optical axis S is shielded by the light shielding layer 32 after passing through the micro convex lens 31. That is, the micro convex lens 31 can concentrate, to the through hole 320 in the light shielding layer 32, small-angle light above that is close to the optical axis and corresponds to the micro convex lens 31. The light reaches the photosensitive pixel 20 below after passing through the through hole 320. Light having a relatively large included angle with the optical axis is shielded by the shielding layer 32 after passing through the micro convex lens 31, but cannot enter the photosensitive pixel 20 to contribute to an image signal. A combination of the light shielding layer 32 and the micro convex lens 31 is equivalent to an optical collimator, and can collimate visible light emitted from the radiation conversion layer 01, and therefore can shield the large-angle light to prevent visible light from being incident on a photosensitive pixel 20 in a deviated position, thereby reducing crosstalk, increasing an image resolution, and improving quality of a detected image.

Further, still referring to the illustration in FIG. 7, values of the solid angles $\theta 1$ and $\theta 2$ are not only related to DH and H, but also related to an area of the through hole 320 and a relative distance between the through hole 320 and the micro convex lens 31.

The area of the through hole 320 can be adjusted to define the maximum solid angle at which light to be collected by the photosensitive pixel 20 deviates from the optical axis. It can be learned from FIG. 7 that, when the area of the through hole 320 is relatively small, the light shielding layer 32 can shield more light having a relatively large angle with the optical axis S. However, this also affects the amount of signals collected by the photosensitive pixel 20, affecting image detection accuracy. Among multiple through holes 320 and multiple micro convex lenses 31 corresponding to one photosensitive pixel 20, some through hole 320 and some micro convex lens 31 that are closer to an edge of the photosensitive pixel 20 can receive more large-angle light emitted from a position corresponding to an adjacent photosensitive pixel 20. With this consideration, those through holes closer to the edge of the photosensitive pixel 20 can be designed with a smaller aperture, and those through holes closer to the center of the photosensitive pixel 20 can be designed with a larger aperture. In other words, the aperture of the through hole 320 is related to the distance from the center of the through hole 320 to the edge of the photosensitive pixel 20, and a smaller distance leads to a smaller aperture. As shown in FIG. 5, an aperture of a through hole 32b near an edge of a photosensitive pixel 20 is less than an aperture of a through hole 32a away from the edge of the photosensitive pixel 20.

In an embodiment, as shown in FIG. 5 and FIG. 7, the microlens layer 03 further includes a substrate layer 33. The substrate layer 33 not only can serve as a substrate that carries the micro convex lenses 31, but also can flatten a surface of an image sensing layer for visible light below. The substrate layer 33 can be made from a material the same as that for manufacturing the micro convex lenses 31, or made from materials that have substantially the same refractive index, so as to reduce reflection when visible light passes through an interface of a film layer. The substrate layer 33 can be made from any of polyimide, polyethylene terephthalate, or acrylic resin.

Figure 8:
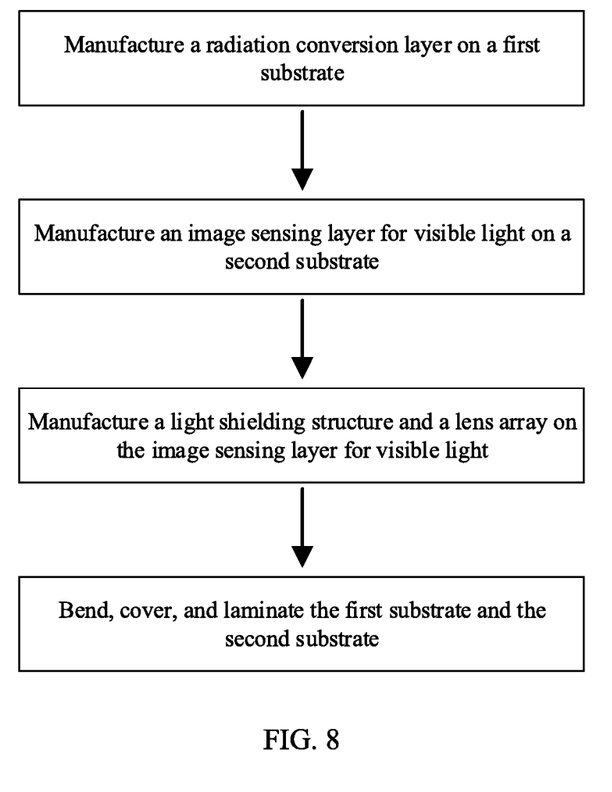
FIG. 8 is a flowchart of a manufacture method for a radiation image detector according to an embodiment of the present invention.

In an embodiment of the present invention, a manufacture method for a radiation image detector is further provided, to manufacture the radiation image detector provided in any of the foregoing embodiments. FIG. 8 is a flowchart of the manufacture method for a radiation image detector according to the embodiment of the present invention. The manufacture method includes the following steps:

manufacturing a radiation conversion layer on a first substrate, the radiation conversion layer being configured to convert a radiation image into a visible light image;

manufacturing an image sensing layer for visible light on a second substrate, the image sensing layer including a pixel array formed by a plurality of photosensitive pixels, and being configured to detect the visible light image;

manufacturing a light shielding structure and a lens array on the image sensing layer, a combination of the light shielding structure and the lens array being capable of controlling light within a certain angle to be incident on the image sensing layer; and bending, covering, and laminating the first substrate and the second substrate. Correspondingly, the radiation conversion layer on the first substrate bends into a bent structure as the first substrate bends. Correspondingly, the image sensing layer and a microlens layer including the light shielding structure and the lens array on the second substrate also bend into bent structures as the second substrate bends.

The first substrate and the second substrate have the same bending direction and bending shape. Correspondingly, the radiation conversion layer, the image sensing layer, and the microlens layer also have the same bending direction and bending shape.

In an embodiment of the present invention, a specific manner of bending the second substrate can include: thinning the second substrate, and placing the thinned second substrate in a bent mold to ensure that the bent second substrate always has a bent structure. Specifically, the second substrate can be a glass substrate, and can be thinned through chemical corrosion or a combination of chemical corrosion and mechanical polishing.

In addition, the bending, covering, and laminating the first substrate and the second substrate specifically includes thinning the second substrate, and placing the thinned second substrate and the bent first substrate in a bent mold for lamination and encapsulation. In this way, the process is easy to implement, and can ensure that the first substrate and the second substrate have mutually adaptive curvature radiuses and therefore can be properly laminated.

In an embodiment of the present invention, a specific manner of bending the second substrate can include: manufacturing one or more layers of metal films on a side, of the second substrate, backing onto the image sensing layer, the metal films having a specific internal expansion or contraction stress. Therefore, the metal films tend to have bending shapes, driving the second substrate to bend. To implement internal expansion or contraction stress, the metal films need to be manufactured at a specific temperature in a vacuum or inert gas environment through vacuum sputtering. The metal films can be made from chromium or molybdenum. Through holes or trenches can be manufactured on the metal films to alleviate the internal stress of the metal films and consequently change the curvature radius of the second substrate, so that the curvature radius of the second substrate meets requirements. The through holes or trenches can be specifically manufactured on the metal films through cutting and peeling using laser. Specifically, the second substrate can be a glass substrate.

In addition, the second substrate can be a flexible material or a rigid material. If the second substrate is a rigid material, the second substrate can be bent through the same process as that of the first substrate.

The manufacture method provided in the embodiment of the present invention can be used to manufacture the radiation image detector on a curved surface provided in the foregoing embodiments. Compared with a conventional flat panel radiation image detector, the radiation image detector on a curved surface has a higher spatial resolution and better spatial uniformity for image luminance and magnifying power.

The foregoing descriptions are merely example embodiments of the present invention, but are not intended to limit the present invention. Any modification, equivalent replacement, or improvement made without departing from the basic concept and principle the embodiments of the present invention should fall within the protection scope of the present invention.

What is claimed is:

1. A radiation image detector, comprising:
a radiation conversion layer, configured to convert a radiation image into a visible light image;
an image sensing layer for visible light, comprising a pixel array formed by a plurality of photosensitive pixels, configured to detect the visible light image; and
a microlens layer, disposed between the radiation conversion layer and the image sensing layer, the microlens layer comprising a lens array formed by a plurality of micro convex lenses, and optical axes of the micro convex lenses being perpendicular to the image sensing layer; the radiation conversion layer, the microlens layer, and the image sensing layer all having curved surface structures which conform to each other and bending in one direction,
wherein the microlens layer further comprises a light shielding structure disposed on the image sensing layer, the light shielding structure comprises at least one light shielding layer, the light shielding layer comprises a plurality of through holes, and the through holes one-to-one correspond to the micro convex lenses; and
wherein each of the photosensitive pixels corresponds to a plurality of micro convex lenses and a plurality of through holes.

2. The radiation image detector according to claim 1, wherein:
an aperture of the through hole is related to the distance from the center of the through hole to an edge of the photosensitive pixel, and a smaller aperture corresponds to a shorter distance.

3. The radiation image detector according to claim 1, wherein:
the center of the through hole overlaps with an optical axis of the micro convex lens corresponding to the through hole.

4. The radiation image detector according to claim 1, wherein:
the curved surface structure is a part of a spherical surface, and curvature radiuses of the radiation conversion layer, the microlens layer, and the image sensing layer are basically the same.

5. The radiation image detector according to claim 4, wherein:
the curvature radius is approximately equal to the distance from the radiation conversion layer to a focal point of an incident radiation, and the focal point is an actual or virtual intersection point of any two incident radiations.

6. A manufacture method for a radiation image detector, comprising:
manufacturing a radiation conversion layer on a first substrate, the radiation conversion layer being configured to convert a radiation image into a visible light image;
manufacturing an image sensing layer for visible light on a second substrate, the image sensing layer comprising a pixel array formed by a plurality of photosensitive pixels, and being configured to detect the visible light image;
manufacturing a light shielding structure and a lens array on the image sensing layer; and
bending, covering, and laminating the first substrate and the second substrate;
wherein the first substrate and the second substrate have the same bending direction and bending shape;
wherein the radiation image detector comprises:
the radiation conversion layer;
the image sensing layer; and
a microlens layer, disposed between the radiation conversion layer and the image sensing layer, the microlens layer comprising a lens array formed by a plurality of micro convex lenses, and optical axes of the micro convex lenses being perpendicular to the image sensing layer; the radiation conversion layer, the microlens layer, and the image sensing layer all having curved surface structures which conform to each other and bending in one direction,
wherein the microlens layer further comprises a light shielding structure disposed on the image sensing layer, the light shielding structure comprises at least one light shielding layer, the light shielding layer comprises a plurality of through holes, and the through holes one-to-one correspond to the micro convex lenses, and
wherein each of the photosensitive pixels corresponds to a plurality of micro convex lenses and a plurality of through holes.

7. The manufacture method according to claim 6, wherein the bending, covering, and laminating the second substrate comprises:
thinning the second substrate, and placing the thinned second substrate and the bent first substrate in a bent mold for lamination and encapsulation.

8. The manufacture method according to claim 6, wherein the bending the second substrate comprises:
manufacturing one or more layers of metal films on a side, of the second substrate, backing onto the image sensing layer, the metal films having a specific internal expansion or contraction stress; and
manufacturing a plurality of openings or trenches on the metal films through laser light or another method to alleviate the internal stress of the metal films, so that the second substrate has a specific bending shape.

* * * * *